(12) United States Patent
Nishitani

(10) Patent No.: US 11,007,164 B2
(45) Date of Patent: May 18, 2021

(54) PREVENTION OR REMEDIATION COMPOSITION FOR DEMENTIA OR DEPRESSION

(71) Applicant: AJINOMOTO CO., INC., Tokyo (JP)

(72) Inventor: Shinobu Nishitani, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/283,919

(22) Filed: Feb. 25, 2019

(65) Prior Publication Data
US 2019/0247347 A1 Aug. 15, 2019

Related U.S. Application Data

(63) Continuation of application No. PCT/JP2017/033174, filed on Sep. 8, 2017.

(30) Foreign Application Priority Data

Sep. 9, 2016 (JP) .............................. JP2016-176295
Sep. 13, 2016 (JP) .............................. JP2016-178739

(51) Int. Cl.
| | |
|---|---|
| *A61K 31/198* | (2006.01) |
| *A61P 25/28* | (2006.01) |
| *A23L 33/175* | (2016.01) |
| *A61P 25/24* | (2006.01) |
| *A61K 31/405* | (2006.01) |
| *A61K 31/4172* | (2006.01) |

(52) U.S. Cl.
CPC .......... *A61K 31/198* (2013.01); *A23L 33/175* (2016.08); *A61K 31/405* (2013.01); *A61K 31/4172* (2013.01); *A61P 25/24* (2018.01); *A61P 25/28* (2018.01); *A23V 2200/322* (2013.01); *A23V 2250/063* (2013.01); *A23V 2250/065* (2013.01); *A23V 2250/0624* (2013.01); *A23V 2250/0626* (2013.01); *A23V 2250/0628* (2013.01); *A23V 2250/0638* (2013.01); *A23V 2250/0648* (2013.01); *A23V 2250/0654* (2013.01)

(58) Field of Classification Search
CPC ............ A23L 33/175; A23V 2200/322; A23V 2250/0624; A23V 2250/0626; A23V 2250/0628; A23V 2250/063; A23V 2250/0638; A23V 2250/0648; A23V 2250/065; A23V 2250/0654; A61K 31/198; A61K 31/405; A61K 31/4172; A61P 25/24; A61P 25/28
See application file for complete search history.

(56) References Cited

U.S. PATENT DOCUMENTS

| | | | | |
|---|---|---|---|---|
| 4,279,917 A | * | 7/1981 | Takami .................. | A61K 38/01 514/400 |
| 5,028,622 A | * | 7/1991 | Plaitakis .............. | A61K 31/195 514/561 |
| 2004/0101934 A1 | * | 5/2004 | Choe ....................... | A23L 33/18 435/91.1 |
| 2007/0286909 A1 | | 12/2007 | Smith et al. | |
| 2008/0275120 A1 | | 11/2008 | Peters et al. | |
| 2010/0105774 A1 | | 4/2010 | Doi | |
| 2011/0183040 A1 | * | 7/2011 | Ermolin .................. | A23L 33/40 426/72 |
| 2011/0245313 A1 | | 10/2011 | Dioguardi | |
| 2013/0116215 A1 | * | 5/2013 | Coma .................. | A61K 31/165 514/108 |

FOREIGN PATENT DOCUMENTS

| | | |
|---|---|---|
| EP | 2 959 895 A1 | 12/2015 |
| JP | 2004-292437 A | 10/2004 |
| JP | 2009-511576 A | 3/2009 |
| JP | 2009-126830 A | 6/2009 |
| RU | 2 151 596 C1 | 6/2000 |
| WO | WO 2008/044691 A1 | 4/2008 |
| WO | WO 2013/073644 A1 | 5/2013 |

OTHER PUBLICATIONS

National Center for Biotechnology Information. "PubChem Compound Summary for CID 6106, Leucine" PubChem, https://pubchem.ncbi.nlm.nih.gov/compound/Leucine. Accessed Sep. 9, 2020. Created Sep. 16, 2004. (Year: 2004).*
Buccafusco et al., "The scopolamine-reversal paradigm in rats and monkeys: the importance of computer-assisted operant-conditioning memory tasks for screening drug candidates", 2008, Psychopharmacology, 199(3), pp. 481-494. (Year: 2008).*
Webster et al., "Using mice to model Alzheimer's dementia: an overview of the clinical disease and the preclinical behavioral changes in 10 mouse models", 2014, FRONTIERS in GENETICS, vol. 5, Article 88, pp. 1-23. (doi: 10.3389/fgene.2014.00088). (Year: 2014).*
Wu et al., "Composition of free and peptide-bound amino acids in beef chuck, loin, and round cuts", 2016, Journal of Animal Science, 94(6), pp. 2603-2613. (Year: 2016).*
International Search Report dated Nov. 28, 2017 in PCT/JP2017/033174, citing documents AA, AJ-AO, and AR-AS therein, 4 pages.
Soi-Ampornkul, R. et al. "Protective effects of pre-germinated brown rice extract against amyloid beta-peptide (1-42)-induced apoptosis in neuronal SK-N-SH cells" Alzheimer's and Dementia, vol. 7, No. 4, 2011, Page S117, abstract P1-018.

(Continued)

*Primary Examiner* — My-Chau T. Tran
(74) *Attorney, Agent, or Firm* — Oblon, McClelland, Maier & Neustadt, L.L.P.

(57) ABSTRACT

Compositions containing one or more kinds of essential amino acids other than leucine and not less than 35 mol % of leucine, relative to the total content of essential amino acids, are useful for preventing or improving dementia or a depressive state, in particular, a depressive state caused by stress, have high safety, and can be continuously ingested or administered.

7 Claims, 10 Drawing Sheets

(56) References Cited

OTHER PUBLICATIONS

Ravaglia, G. et al. "Plasma amino acid concentrations in healthy and cognitively impaired oldest-old individuals: associations with anthropometric parameters of body composition and functional disability" British Journal of Nutrition, vol. 88, No. 5, 2002, pp. 563-572.

Rondanelli, M. et al. "Mild cognitive impairment in elderly and supplementation with omega 3 fatty acids, melatonin and tryptophan: a review" AgroFOOD industry hi-tech, vol. 22, No. 4, 2011, pp. 23-24.

Ohtsuka, Y. et al. "Effect of Oral Administration of L-Arginine on Senile Dementia" The American Journal of Medicine, vol. 108, No. 5, 2000, p. 439.

Rubey, R.N. et al. "Could lysine supplementation prevent Alzheimer's dementia? A novel hypothesis" Neuropsychiatric Disease and Treatment, vol. 6, 2010, pp. 707-710.

Da Silva, J. et al. "Affective disorders and risk of developing dementia: systematic review" The British Journal of Psychiatry, vol. 202, No. 3, 2013, pp. 177-186.

Simões Do Couto, F. et al. "Depression with melancholic features is associated with higher long-term risk for dementia" Journal of Affective Disorders, vol. 202, 2016, pp. 220-229.

Extended European Search Report dated Feb. 12, 2020 in European Patent Application No. 17848918.3, citing documents AA and AO therein, 7 pages.

* cited by examiner

Fig. 8

KN209 stress load menu

| | | | | | |
|---|---|---|---|---|---|
| 5 | | | 1 arrival | 2 restraint | 3 forced swimming | 4 |
| | 6 9:00-17:00 food fasting body weight, feeding | 7 17:00-9:00 cage slope (45°) | 8 17:00-9:00 water-soaked cage | 9 9:00-21:00 lighting on | 10 forced swimming | 11 |
| 12 | 13 water-soaked cage body weight, feeding | 14 9:00-17:00 food fasting | 15 17:00-9:00 cage slope (45°) | 16 cage exchange | 17 restraint | 18 |
| 19 | 20 forced swimming body weight, feeding | 21 17:00-9:00 water-soaked cage | 22 17:00-9:00 cage slope (45°) | 23 cage exchange | 24 restraint | 25 |
| 26 | 27 9:00-21:00 lighting on sucrose habituation body weight, feeding | 28 17:00-9:00 water-soaked cage Y maze sucrose habituation | 29 6hr water deprivation sucrose test 17:00-9:00 cage slope (45°) | 30 forced swimming | 7/1 autopsy body weight | |

PREVENTION OR REMEDIATION COMPOSITION FOR DEMENTIA OR DEPRESSION

CROSS REFERENCES TO RELATED APPLICATIONS

This application is a continuation of International Patent Application No. PCT/JP2017/033174, filed on Sep. 8, 2017, and claims priority to Japanese Patent Application No. 2016-176295, filed on Sep. 9, 2016, and Japanese Patent Application No. 2016-178739, filed on Sep. 13, 2016, all of which are incorporated herein by reference in their entireties.

BACKGROUND OF THE INVENTION

Field of the Invention

The present invention relates to compositions for preventing or improving dementia or a depressive state, in particular, a depressive state caused by stress. The present invention also relates to methods for preventing or improving dementia or a depressive state, in particular, a depressive state caused by stress.

Discussion of the Background

With the recent rapid increase in the elderly population, the number of patients with dementia has increased rapidly, and it has been reported that the population with dementia reached 8.4% of the population of those aged 65 or over in 2015.

According to the Ministry of Health, Labor and Welfare, in Japan, dementia is defined to mean "a state in which various mental functions that once developed normally after the birth have chronically declined and disappeared to the extent that daily life and social life cannot be managed".

Dementia includes dementia caused by various diseases such as Alzheimer-type dementia, frontotemporal dementia (Pick disease etc.), Lewy body dementia, and cerebrovascular dementia. While aging is the greatest risk factor, its cause is often unclear.

However, in any type of dementia, core symptoms such as memory disorder, disorientation and the like, and behavioral and psychological symptoms such as behavior abnormality, mental symptoms and the like are commonly observed, and progression of symptoms has serious effects such as increased burden of nursing care and the like for not only patients but also their families.

Currently, acetylcholinesterase inhibitors such as donepezil hydrochloride, and NMDA (N-methyl-D-aspartate) receptor antagonists such as memantine have been approved as therapeutic drugs for dementia. However, these therapeutic drugs for dementia are basically for Alzheimer-type dementia, are symptomatic treatment drugs, and can merely suppress progression of the symptoms somewhat.

Regarding the prevention of dementia, the importance of meal and exercise is known.

Regarding meals, the effectiveness of antioxidants such as vitamin C, vitamin E, β-carotene and ω-3 long-chain unsaturated fatty acids has been reported, and the effects of ingestion of ω-3 long-chain unsaturated fatty acid, melatonin and tryptophan on mild cognitive impairment of the elderly people have been studied (see Angro Food Industry Hi-Tech 22 (4) 23-24 (2011), which is incorporated herein by reference in its entirety). Furthermore, reports suggest the effect of L-arginine and lysine on Alzheimer-type dementia (see The American Journal of Medicine 108 (5) 439 (2000 Apr. 1) and Neuropsychiatric Disease and Treatment 6 707-710 (2010), both of which are incorporated herein by reference in their entireties).

Regarding exercise, it has been found that an increase in cerebral blood flow due to exercise can improve physical activity and prevent Alzheimer's disease.

However, some of the above-mentioned ingredients ingested in meals do not have sufficient preventive effect against dementia, and many require future verification of the effectiveness.

Furthermore, some middle-aged and elderly people who have an increased risk of developing dementia often have difficulty in exercising due to disease or the like, or may have difficulty, due to a decline of physical function, in continuing exercise for prevention of Alzheimer's disease.

Therefore, it is difficult to say that a preventive drug having an effective preventive effect on dementia, having high safety and capable of continuous ingestion, or a therapeutic drug capable of improving dementia has been obtained.

Depressive state or depression refers to a situation in which the mood is depressed to dislike activity, due to which thought, behavior, emotion, and happiness are influenced.

Many depressive states are caused by various stresses, for example, job problems such as job loss, career change, and human relations at home or workplace. It is also known to be sometimes caused by endocrine diseases such as hypothyroidism, diseases such as diabetes, cancer, sleep apnea syndrome, and medicaments such as interferon preparation, corticosteroid drug.

A temporary depressive state can be improved by overcoming the stress causing the state. Thus, a depressive state or depression is not generally treated with an antidepressant and the like.

However, when stress is a serious one that cannot be solved easily and continues for a long time, it may progress to a pathological depressive state such as clinical depression.

Furthermore, depression is a symptom that appears as one of the behavioral and psychological symptoms of dementia (BPSD). It is also known that a depressive state is a high risk factor of the onset of dementia (see The British Journal of Psychiatry 202 177-186 (2013) and Journal of Affective Disorders 202 220-229 (2016), both of which are incorporated herein by reference in their entireties).

Accordingly, a composition for preventing or improving a depressive state is desired, which is capable of preventing or improving a depressive state, in particular, a depressive state caused by stress, and has high safety.

SUMMARY OF THE INVENTION

Accordingly, it is one object of the present invention to provide novel compositions for preventing or improving dementia, which have an effective preventive or improving effect on dementia, are highly safe, and enable continuous ingestion.

It is another object of the present invention to provide novel compositions for preventing or improving a depressive state, which can favorably prevent or improve a depressive state, particularly a depressive state caused by stress, have high safety and permit continuous ingestion or administration.

It is another object of the present invention to provide novel methods for preventing or improving dementia by administering such a composition.

These and other objects, which will become apparent during the following detailed description, have been achieved by the inventor's discovery that compositions containing a high content of leucine, and one or more kinds of essential amino acids other than leucine have an effect of improving memory disorder and cognitive function, and are effective for preventing or improving dementia.

Furthermore, the present inventor has found that a composition containing a high content of leucine, and one or more kinds of essential amino acids other than leucine has a preventive or improving effect on a depressive state, particularly, a depressive state caused by stress.

That is, the present invention provides the following.

(1) A composition for preventing or improving dementia, comprising one or more kinds of essential amino acids other than leucine and not less than 35 mol % of leucine relative to the total content of essential amino acids.

(2) The composition of (1), wherein the content of leucine is 35 mol % to 66 mol % relative to the total content of essential amino acids.

(3) The composition of (1) or (2), wherein one or more kinds of essential amino acids other than leucine are isoleucine, valine, threonine, lysine, methionine, histidine, phenylalanine, and tryptophan.

(4) The composition of (3), wherein a molar composition ratio of the content of each amino acid relative to the total content of essential amino acids falls within the following numerical values:
leucine 35 mol % to 66 mol %
isoleucine 5 mol % to 15 mol %
valine 5 mol % to 15 mol %
threonine 7 mol % to 14 mol %
lysine 8 mol % to 16 mol %
methionine 2 mol % to 10 mol %
histidine 0.1 mol % to 3.5 mol %
phenylalanine 2.5 mol % to 8 mol %
tryptophan 0.1 mol % to 2 mol %.

(5) The composition of any of (1) to (4), wherein the composition prevents or improves a memory disorder.

(6) The composition of any of (1 to (4), wherein the composition suppresses a decline of cognitive function or improves cognitive function.

(7) The composition of any of (1) to (6), wherein the composition is a pharmaceutical product.

(8) The composition of any of (1) to (6), wherein the composition is a food.

(9) The composition of any of (1) to (8), wherein the dementia is Alzheimer-type dementia.

(10) A method for preventing or improving dementia, comprising ingestion by or administration to a subject in need of prevention or improvement of symptoms of dementia of an effective amount of a composition comprising one or more kinds of essential amino acids other than leucine and not less than 35 mol % of leucine relative to the total content of essential amino acids.

(11) The method of (10), wherein a content of leucine is 35 mol % to 66 mol % relative to the total content of essential amino acids.

(12) The method of (10) or (11), wherein one or more kinds of essential amino acids other than leucine are isoleucine, valine, threonine, lysine, methionine, histidine, phenylalanine, and tryptophan.

(13) The method of any of (10) to (12), wherein the dementia is Alzheimer-type dementia.

(14) A composition for preventing or improving a depressive state, comprising one or more kinds of essential amino acids other than leucine, and not less than 35 mol % of leucine relative to the total content of essential amino acids.

(15) The composition of (14), wherein the content of leucine is 35 mol % to 66 mol % relative to the total content of the essential amino acids.

(16) The composition of (14) or (15), wherein one or more kinds of essential amino acid other than leucine includes isoleucine, valine, threonine, lysine, methionine, histidine, phenylalanine, and tryptophan.

(17) The composition of (16), wherein a molar composition ratio of each amino acid to the total content of the essential amino acids is within the following numerical range:
leucine: 35 mol % to 66 mol %
isoleucine: 5 mol % to 15 mol %
valine: 5 mol % to 15 mol %
threonine: 7 mol % to 14 mol %
lysine: 8 mol % to 16 mol %
methionine: 2 mol % to 10 mol %
histidine: 0.1 mol % to 3.5 mol %
phenylalanine: 2.5 mol % to 8 mol %
tryptophan: 0.1 mol % to 2 mol %.

(18) The composition of any of (14) to (17), wherein the depressive state is a depressive state caused by stress.

(19) The composition of any of (14) to (18), wherein the composition is a pharmaceutical product.

(20) The composition of any of (14) to (18), wherein the composition is a food.

(21) A method for preventing or improving a depressive state, comprising ingestion by or administration to a subject in need of prevention or improvement of a depressive state of an effective amount of a composition comprising one or more kinds of essential amino acids other than leucine and not less than 35 mol % of leucine relative to the total content of the essential amino acids.

(22) The method of (21), wherein the content of leucine is 35 mol % to 66 mol % of the total content of the essential amino acids.

(23) The method of (21) or (22), wherein one or more kinds of essential amino acids other than leucine include isoleucine, valine, threonine, lysine, methionine, histidine, phenylalanine, and tryptophan.

(24) The method of any of (21) to (23), wherein the depressive state is a depressive state caused by stress.

Effect of the Invention

According to the present invention, a composition for preventing or improving dementia can be provided.

The composition for preventing or improving dementia of the present invention effectively prevents or improves memory disorders, is also effective for the suppression or improvement of a decline of cognitive function, and particularly effective for preventing or improving Alzheimer-type dementia.

Furthermore, the composition for preventing or improving dementia of the present invention is highly safe and suitable for continuous ingestion or administration.

According to the present invention, a composition for preventing or improving a depressive state, which can favorably prevent or improve the depressive state can be provided.

The composition for preventing or improving a depressive state of the present invention is particularly effective for preventing or improving a depressive state caused by stress.

Furthermore, the composition for preventing or improving a depressive state of the present invention has high safety and is suitable for continuous ingestion or administration.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 8 shows a stress load menu in Experimental Example 2.

DETAILED DESCRIPTION OF THE PREFERRED EMBODIMENTS

Figure 1:
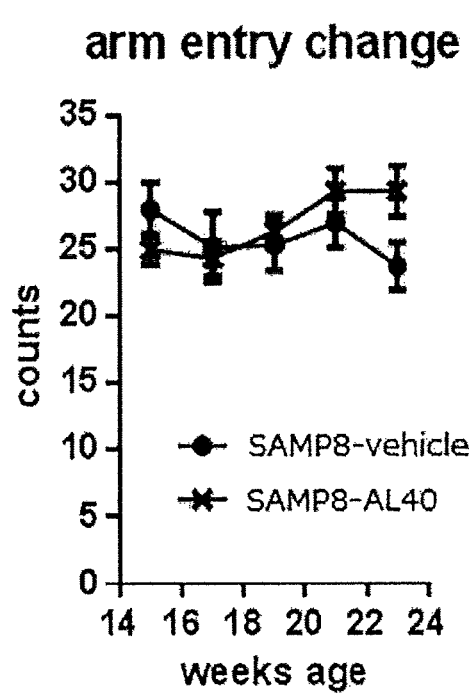
FIG. 1 shows age-related changes in the total number of entries into the arm in the group in which deionized water was orally administered to SAMP8 (SAMP8-vehicle) and the group in which the composition of Example 1 was orally administered to SAMP8 (SAMP8-AL40) in the Y maze test in Experimental Example 1.

The composition for preventing or improving dementia of the present invention (hereinafter to be also referred to as "the composition for dementia of the present invention" in the present specification) contains one or more kinds of essential amino acids other than leucine (i.e., one or more kinds selected from the group consisting of isoleucine, valine, threonine, lysine, methionine, histidine, phenylalanine, and tryptophan), and not less than 35 mol % of leucine relative to the total content of essential amino acids.

In the present specification, "dementia" refers to a condition in which any of the symptoms of memory disorder, decline of cognitive function (orientation disorder), lower judgment and deficit in executive function is presented as the core symptom, and also includes various behavioral and psychological symptoms of dementia (BPSD) such as depressive state, dependence, anxiety, aggressive behavior, hallucination, delusion, sleep disorder, wandering and the like.

It also includes dementia caused by various diseases and lesions such as Alzheimer's disease, Frontotemporal lobar degeneration (Pick disease etc.), Lewy body disease, and cerebrovascular diseases.

The term "prevention of dementia" refers to suppression of the onset of dementia showing the above-mentioned symptom or state, and "improvement of dementia" refers to reduction of the above-mentioned symptoms or conditions.

The composition for preventing or improving a depressive state of the present invention (hereinafter to be also referred to as "the composition for depressive state of the present invention" in the present specification) contains one or more kinds of essential amino acids other than leucine (i.e., one or more kinds selected from the group consisting of isoleucine, valine, threonine, lysine, methionine, histidine, phenylalanine and tryptophan), and not less than 35 mol % of leucine relative to the total content of essential amino acids.

In the present specification, the "depressive state" refers to a state in which the mood is depressed and dislikes activity, due to which thought, behavior, emotion, and happiness are influenced.

Specifically, it is a state having as a main complaint at least one of "apathy", "feeling blue", "feeling tired both physically and mentally", "unable to get out of sorrow", "unable to concentrate on thinking, unable to concentrate, or unable to make judgment", "irritated or unable to stay calm", "feeling miserable or caught by sense of inferiority", "heavy head or heavy body", "waking up feeling bad, or unable to wake up in the morning", "having difficulty falling asleep, unable to sleep", "unable to read books or newspapers, or unable to understand even after reading", "not wanting to meet people, wanting to stay home without going anywhere, feeling troublesome to move", "feeling lonely, feeling anxiety, feeling alienated, or feeling strange", "no appetite, or not feeling food delicious", "feeling painful, feeling despair, or wishing to die" and the like.

The cause of depressive state includes bereavement and separation from closest family member or pets, distress in human relations, job change, job transfer, promotion, personnel reshuffle, compulsory retirement, restructuring, business bankruptcy, failure in academic work or job, discouragement, romantic breakup, divorce, child independence, illness, overwork, accident, climacteric disorder, pregnancy, childbirth, moving, construction of new house, sudden change in living environment, affliction, internal stress from growing history and life history, mental or physical stress from age-related degradation of physical and mental functions and the like; physical disease such as brain disorder, chronic disease, endocrine disease and the like; side effects of medicaments such as interferon preparation, adrenal cortical steroid drug (prednisone etc.), and antihypertensive agent (valsartan, amlodipine besylate, etc.), and the like.

The term "prevention of a depressive state" refers to suppression of appearance of the depressive state described above, and "improvement of a depressive state" refers to reduction of symptoms or level of the observed depressive state.

In the present invention, "leucine" and "essential amino acid other than leucine" used may be any of an L form, a D form and a DL form. An L form and a DL form are preferably used, and an L form is more preferably used.

In the present invention, "leucine" and "essential amino acid other than leucine" can be used not only in a free form but also a salt form. The term "leucine" and "essential amino acid other than leucine" in the present specification are concepts each encompassing even a salt. The salt form is not particularly limited as long as it is a pharmacologically acceptable salt, and acid addition salt, salt with base and the like can be mentioned.

Concrete examples include salts with inorganic bases, salts with organic bases, salts with inorganic acids, salts with organic acids, salts with amino acid and the like.

Examples of the salts with inorganic bases include salts with alkali metals such as lithium, sodium, potassium and the like, salts with alkaline earth metals such as magnesium, calcium and the like, ammonium salt and the like.

Examples of the salts with organic bases include salts with alkanolamine such as monoethanolamine, diethanolamine, triethanolamine and the like, salts with heterocyclic amine such as morpholine, piperidine and the like, and the like.

Examples of the salts with inorganic acids include salts with hydrohalic acid (hydrochloric acid, hydrobromic acid, hydroiodic acid etc.), sulfuric acid, nitric acid, phosphoric acid and the like.

Examples of the salts with organic acids include salts with monocarboxylic acid such as formic acid, acetic acid, propanoic acid and the like; salts with saturated dicarboxylic acid such as oxalic acid, malonic acid, malic acid, succinic acid and the like; salts with unsaturated dicarboxylic acid such as maleic acid, fumaric acid and the like; salts with tricarboxylic acid such as citric acid and the like; salts with keto acid such as α-ketoglutaric acid and the like.

Examples of the salts with amino acid include salts with aliphatic amino acid such as glycine, alanine and the like; salts with aromatic amino acid such as tyrosine and the like; salts with basic amino acid such as arginine and the like; salts with acidic amino acid such as aspartic acid, glutamic acid and the like; salts with amino acid forming lactam such as pyroglutamic acid and the like; and the like.

The above-mentioned salts may each be a hydrate (salt hydrate), and examples of the hydrate include 1 hydrate to 6 hydrate and the like.

In the present invention, one kind each of "leucine" and "essential amino acid other than leucine" in the above-mentioned free form or salt form may be used singly, or two or more kinds thereof may be used in combination.

For the object of the present invention, a free form, hydrochloride or the like of each of "leucine" and "essential amino acid other than leucine" is preferable.

In the present invention, the above-mentioned each amino acid in a free form or salt form to be used may be extracted from animals, plants or the like, which are naturally present, and purified, or obtained by a chemical synthesis method, a fermentation method, an enzyme method or a gene recombinant method and the like. Commercially available products provided by each company may also be utilized.

In the composition for dementia of the present invention, leucine is contained at a high content of not less than 35 mol % relative to the total content of essential amino acids.

In the present specification, the content of each amino acid such as leucine in the composition for dementia of the present invention when it is contained in a salt form is shown by the content converted to that of a free form.

From the aspect of the effect of preventing or improving dementia, the content of leucine is preferably 35 mol % to 66 mol %, more preferably 35 mol % to 57 mol %, further preferably 35 mol % to 50 mol %, relative to the total content of essential amino acids.

The content of isoleucine contained as essential amino acid other than leucine is preferably 5 mol % to 15 mol % relative to the total content of the essential amino acids.

The content of valine contained as essential amino acid other than leucine is preferably 5 mol % to 15 mol % relative to the total content of the essential amino acids.

The content of threonine contained as essential amino acid other than leucine is preferably 7 mol % to 14 mol % relative to the total content of the essential amino acids.

The content of lysine contained as essential amino acid other than leucine is preferably 8 mol % to 16 mol % relative to the total content of the essential amino acids.

The content of methionine contained as essential amino acid other than leucine is preferably 2 mol % to 10 mol % relative to the total content of the essential amino acids.

The content of histidine contained as essential amino acid other than leucine is preferably 0.1 mol % to 3.5 mol % relative to the total content of the essential amino acids.

The content of phenylalanine contained as essential amino acid other than leucine is preferably 2.5 mol % to 8 mol % relative to the total content of the essential amino acids.

The content of tryptophan contained as essential amino acid other than leucine is preferably 0.1 mol % to 2 mol % relative to the total content of the essential amino acids.

From the aspect of the effect of preventing or improving dementia, the composition for dementia of the present invention more preferably contains isoleucine, valine, threonine, lysine, methionine, histidine, phenylalanine and tryptophan at the above-mentioned contents as essential amino acids other than leucine.

In the composition for depressive state of the present invention, leucine is contained at a high content of not less than 35 mol % relative to the total content of essential amino acids.

In the present specification, the content of each amino acid such as leucine in the composition for depressive state of the present invention when it is contained in a salt form is shown by the content converted to that of a free form.

From the aspect of a preventive or improving effect on a depressive state, the content of leucine is preferably 35 mol % to 66 mol %, more preferably 35 mol % to 57 mol %, further preferably 35 mol % to 50 mol %, relative to the total content of essential amino acids.

The content of isoleucine contained as essential amino acid other than leucine is preferably 5 mol % to 15 mol % relative to the total content of the essential amino acids.

The content of valine contained as essential amino acid other than leucine is preferably 5 mol % to 15 mol % relative to the total content of the essential amino acids.

The content of threonine contained as essential amino acid other than leucine is preferably 7 mol % to 14 mol % relative to the total content of the essential amino acids.

The content of lysine contained as essential amino acid other than leucine is preferably 8 mol % to 16 mol % relative to the total content of the essential amino acids.

The content of methionine contained as essential amino acid other than leucine is preferably 2 mol % to 10 mol % relative to the total content of the essential amino acids.

The content of histidine contained as essential amino acid other than leucine is preferably 0.1 mol % to 3.5 mol % relative to the total content of the essential amino acids.

The content of phenylalanine contained as essential amino acid other than leucine is preferably 2.5 mol % to 8 mol % relative to the total content of the essential amino acids.

The content of tryptophan contained as essential amino acid other than leucine is preferably 0.1 mol % to 2 mol % relative to the total content of the essential amino acids.

From the aspect of a preventive or improving effect on a depressive state, the composition for depressive state of the present invention more preferably contains isoleucine, valine, threonine, lysine, methionine, histidine, phenylalanine, and tryptophan at the above-mentioned contents as essential amino acids other than leucine.

The composition for dementia or composition for depressive state of the present invention may further contain other nutrition components such as carbohydrate, lipid, protein, non-essential amino acid, vitamin, mineral and the like, in addition to the above-mentioned essential amino acids.

The composition for dementia or composition for depressive state of the present invention can be formulated into various forms such as liquids such as solution, suspension, emulsion and the like; semi-solid such as gel, cream and the like; solid such as powder, granule, tablet, capsule and the like, and the like by adding other nutrition components and pharmaceutically acceptable additives to leucine and essential amino acid other than leucine as necessary and according to a formulating means well known in the field of preparations, for example, the methods described in the Japanese Pharmacopoeia XVII General Rules for preparations [3] Monographs for Preparations, which is incorporated herein by reference in its entirety, and the like.

The above-mentioned pharmaceutically acceptable additive can be appropriately selected according to the form of the composition for dementia or composition for depressive state of the present invention and, for example, excipient, binder, disintegrant, lubricant, coating agent, base, solvent, solubilizing agents, solubilizer, emulsifier, dispersing agent, suspending agent, stabilizer, thickener, soothing agent, isotonicity agent, pH adjuster, antioxidant, antiseptic, preservative, corrigent, sweetening agent, flavor, colorant and the like can be mentioned.

To be specific, examples of the excipient include magnesium carbonate, saccharides (glucose, lactose, cornstarch, etc.), sugar alcohol (sorbitol, mannitol, etc.) and the like.

Examples of the binder include gelatin, pregelatinized starch, partly pregelatinized starch, cellulose and a derivative thereof (crystalline cellulose, hydroxypropylcellulose, etc.) and the like.

Examples of the disintegrant include crospovidone, povidone, crystalline cellulose and the like.

Examples of the lubricant include talc, magnesium stearate and the like.

Examples of the coating agent include methacrylic acid-methyl methacrylate copolymer, methacrylic acid-ethyl acrylate copolymer, methyl methacrylate-butyl methacrylate-dimethylaminoethyl methacrylate copolymer, ethyl acrylate-methyl methacrylate-trimethylammonioethylmethacrylatechrolide copolymer and the like.

Examples of the base include animal and plant fats and oils (olive oil, cacao butter, beef tallow, sesame oil, hydrogenated oil, castor oil etc.), wax (Carnauba wax, beeswax, etc.), polyethylene glycol and the like.

Examples of the solvent include purified water, water for injection, monovalent alcohol (ethanol etc.), polyhydric alcohol (glycerol etc.) and the like.

Examples of the solubilizing agent include propylene glycol, medium-chain triglyceride and the like.

Examples of the solubilizer, emulsifier, dispersing agent and suspending agent include surfactant and the like such as sorbitan fatty acid ester, glycerol fatty acid ester, polyoxyethylene sorbitan fatty acid ester (polysorbate 20, polysorbate 80, etc.), polyoxyethylene hydrogenated castor oil, sucrose fatty acid ester and the like.

Examples of the stabilizer include adipic acid, β-cyclodextrin, ethylenediamine, sodium edetate and the like.

Examples of the thickener include water-soluble polymer (sodium polyacrylate, carboxyvinyl polymer, etc.), polysaccharides (sodium alginate, xanthan gum, tragacanth, etc.) and the like.

Examples of the soothing agent include ethyl aminobenzoate, chlorobutanol, propylene glycol, benzyl alcohol and the like.

Examples of the isotonicity agent include potassium chloride, sodium chloride, sorbitol, saline and the like.

Examples of the pH adjuster include hydrochloric acid, sulfuric acid, acetic acid, citric acid, lactic acid, sodium hydroxide, potassium hydroxide and the like.

Examples of the antioxidant include dibutylhydroxytoluene (BHT), butylhydroxyanisole (BHA), dl-α-tocopherol, erythorbic acid and the like.

Examples of the antiseptic and preservative include paraben (methylparaben etc.), benzyl alcohol, sodium dehydroacetate, sorbic acid and the like.

Examples of the corrigent include ascorbic acid, erythritol, L-sodium glutamate and the like.

Examples of the sweetening agent include aspartame, licorice extract, saccharin and the like.

Examples of the flavor include l-menthol, d-camphor, vanillin and the like.

Examples of the colorant include tar pigment (Food Color Red No. 2, Food Color Blue No. 1, Food Color yellow No. 4, etc.), inorganic pigment (red iron oxide, yellow iron oxide, black iron oxide, etc.), natural dye (turmeric extract, β-carotene, sodium copper-chlorophyllin, etc.) and the like.

In the present invention, one or more kinds of the above-mentioned additive can be used.

The daily ingestion amount or dose of the composition for dementia of the present invention is appropriately determined according to the sex, age of the subject to be applied to (hereinafter to be also referred to as the "application subject" in the present specification), symptom or level of dementia observed in the application subject, the form of the composition for dementia of the present invention, administration method and the like. When the application subject is a human adult, it is generally 0.5 g to 22 g, preferably 1 g to 20 g, more preferably 3 g to 16 g, as the total amount of leucine and essential amino acid other than leucine (the total amount converted to the amount of free form).

The above-mentioned amount can be ingested or administered at once or in several portions (e.g., 2 to 4 portions) per day.

In addition, the ingestion or dosing period of the composition for dementia of the present invention is also appropriately determined according to the condition and symptoms of the application subject, and the like. Considering that dementia develops along with aging, various diseases, lesions in the brain, and the like and progresses chronically, continuous ingestion or administration for a long period of time is preferable to prevent or improve dementia.

The daily ingestion amount or dose of the composition for depressive state of the present invention is appropriately determined according to the sex, age of the application subject, symptom or level of depressive state observed in the application subject, the form of the composition for depressive state of the present invention, administration method and the like. When the application subject is a human adult, it is generally 0.5 g to 22 g, preferably 1 g to 20 g, more preferably 3 g to 16 g, as the total amount of leucine and essential amino acid other than leucine (the total amount converted to the amount of free form).

The above-mentioned amount can be ingested or administered at once or in several portions (e.g., 2 to 3 portions) per day.

In addition, the ingestion or dosing period of the composition for depressive state of the present invention is also appropriately determined according to the condition and symptoms of the depressive state of the application subject, and the like. Considering that a depressive state is often caused by stress that is routinely applied, it is preferable to use the composition of the present invention for continuous ingestion or administration for a long period of time in order to prevent or improve a depressive state.

The composition for dementia or composition for depressive state of the present invention can be formulated as a unit package form. In the present specification, the "unit package foam" means a form of one or more units with a particular amount (e.g., ingestion amount or dose per one time etc.) as one unit is/are filled in one container or packed in a package. For example, a unit package form with ingestion amount or dose per one time as one unit is referred to as "unit package form for ingestion amount or dose per one time". A container or package used for the unit package form can be appropriately selected according to the form and the like of the composition for dementia or composition for depressive state of the present invention. For example, paper container or bag, plastic container or bag, pouch, aluminum can, steel can, glass bottle, pet bottle, PTP (press through pack) package sheet and the like can be mentioned.

The application subject of the composition for dementia or composition for depressive state of the present invention includes, for example, mammals (e.g., human, monkey, mouse, rat, guinea pig, hamster, rabbit, cat, dog, bovine, horse, donkey, swine, sheep, etc.), birds (e.g., duck, chicken, goose, turkey, etc.) and the like.

When the composition for dementia or composition for depressive state of the present invention is applied to an application subject animal (hereinafter to be also simply referred to as "subject animal") other than human, the ingestion amount or dose of the composition for dementia or composition for depressive state of the present invention can be appropriately set according to the kind, sex, body weight and the like of the subject animal.

Of the symptoms seen as core symptoms of dementia, the composition for dementia of the present invention more effectively prevents or improves memory disorders and is more effective in suppressing or improving a decline of cognitive function. In addition, it is particularly effective for preventing or improving Alzheimer-type dementia in which the content of acetylcholine, a neurotransmitter in the brain, decreases.

Furthermore, since the composition for dementia of the present invention is contained in foods and contains amino acids with abundant food experience as active ingredients, it is highly safe, suitable for continuous ingestion, and thus useful for preventing or improving dementia.

Therefore, the composition for dementia of the present invention is preferably ingested by or administered to patients showing symptoms of dementia, patients with a risk of developing dementia, and elderly people and middle- or late middle-aged persons who require prevention of dementia.

The composition for dementia of the present invention may be particularly preferably ingested or administered by patients showing symptoms of Alzheimer-type dementia, patients who may develop the aforementioned dementia, elderly people and middle- or late middle-aged persons having a high onset risk of Alzheimer-type dementia, and the like.

The composition for depressive state of the present invention is effective for preventing or improving a depressive state caused by various factors, and particularly affords a good preventive or improving effect on a depressive state caused by mental or physical stress.

In addition, since the composition for depressive state of the present invention is contained in foods and contains amino acids with abundant food experience as active ingredients, it is highly safe, suitable for continuous ingestion or administration, and thus useful for preventing or improving a depressive state caused by stress applied routinely.

Therefore, the composition for depressive state of the present invention may be preferably ingested or administered by those showing a depressive state, as well as those with high possibility of developing a depressive state such as elderly people suffering from age-related decline in physical function or mental function, and middle- or late middle-aged persons who often suffer from various stresses in workplace, home, and the like.

The composition for dementia of the present invention can be provided as a pharmaceutical product (hereinafter to be also referred to as "the pharmaceutical product for dementia of the present invention" in the present specification) directly or by further adding the above-mentioned pharmaceutically acceptable additives.

The pharmaceutical product for dementia of the present invention can have a dosage form of oral preparation such as tablet, coating tablet, chewable tablet, pill, (micro)capsule, granule, fine granule, powder, elixir, lemonade, syrup, suspension, emulsion, oral jelly and the like, injection such as solution, suspension, emulsion and the like, solid injection to be used by dissolving or suspending when in use, injectable preparation such as transfusion, sustainable injection and the like, tubal liquid, and the like.

The pharmaceutical product for dementia of the present invention may contain an anti-dementia drug as long as the characteristics of the present invention are not impaired.

Examples of the anti-dementia drug include acetylcholinesterase inhibitors such as donepezil hydrochloride, galanthamine, rivastigmine and the like; and NMDA receptor antagonists such as memantine and the like, and these can be used according to general dosage.

The pharmaceutical product for dementia of the present invention may be preferably administered to patients with dementia, patients who may develop dementia, elderly people and middle- or late middle-aged persons having a high onset risk of dementia, and the like.

The pharmaceutical product for dementia of the present invention is administered to the above-mentioned application subject such that the total amount per day of leucine and essential amino acid other than leucine is the above-mentioned dose per day.

The composition for depressive state of the present invention can be provided as a pharmaceutical product (hereinafter to be also referred to as "the pharmaceutical product for depressive state of the present invention" in the present specification) directly or by further adding the above-mentioned pharmaceutically acceptable additives.

The pharmaceutical product for depressive state of the present invention can have a dosage form of oral preparation such as tablet, coating tablet, chewable tablet, pill, (micro) capsule, granule, fine granule, powder, elixir, lemonade, syrup, suspension, emulsion, oral jelly and the like, injection such as solution, suspension, emulsion and the like, solid injection to be used by dissolving or suspending when in use, injectable preparation such as transfusion, sustainable injection and the like, tubal liquid, and the like.

The pharmaceutical product for depressive state of the present invention may contain an antidepressant as long as the characteristics of the present invention are not impaired.

Examples of the antidepressant include tricyclic antidepressants such as imipramine hydrochloride, clomipramine hydrochloride, trimipramine maleate and the like; tetracyclic antidepressants such as maprotiline hydrochloride, mianserin hydrochloride, setiptiline maleate and the like; selective serotonin reuptake inhibitors such as fluvoxamine maleate, paroxetine hydrochloride hydrate and the like; selective serotonin-noradrenaline reuptake inhibitors such as milnacipran hydrochloride and the like. These can be used according to a general dosage.

The pharmaceutical product for depressive state of the present invention may be preferably administered to those showing a depressive state and those with high possibility of developing a depressive state by being exposed to various stresses.

The pharmaceutical product for depressive state of the present invention is administered to the above-mentioned application subject such that the total amount per day of leucine and essential amino acid other than leucine is the above-mentioned dose per day.

Furthermore, the composition for dementia of the present invention can be ingested by adding to various foods. The food to which the composition of the present invention is added is not particularly limited, and may be any as long as it is a food in the form generally served for meals or dessert.

For example, the composition for dementia of the present invention is added to drinks such as beverage water and the like, and a suitable flavor is added when desired, whereby a drink can be provided.

More specifically, the composition for dementia of the present invention can be added, for example, to beverage water such as fruit juice drinks, sport drinks and the like; dairy products such as milk, yogurt and the like; confectionery such as jelly, chocolate, candy and the like, and the like.

The composition for dementia of the present invention is preferably added to the above-mentioned various foods in amounts to be ingested per day such that the total amount of leucine and essential amino acid other than leucine is the above-mentioned dose per day.

The composition for dementia of the present invention can be provided as a food (hereinafter to be also referred to as "the food for dementia of the present invention" in the present specification) directly or by adding general food additives as necessary and according to a general food production technique.

The food for dementia of the present invention can be prepared as various forms such as liquid, suspension, emulsified liquid, gel, cream, powder, granule, sheet, capsule, tablet and the like.

Furthermore, the food for dementia of the present invention can be prepared as various food forms such as beverage water (fruit juice drinks, sport drinks, coffee drinks, tea drinks, etc.), dairy product (lactic fermenting beverage, fermented milk, butter, cheese, yogurt, processed milk, defatted milk, etc.), meat product (ham, sausage, hamburger, etc.), fish meat processed seafood paste product (fish cake, tube-shaped fish sausage, deep-fried ball of fish paste, etc.), egg product (rolled Japanese-style omelette, steamed egg custard, etc.), confectionery (cookie, jelly, chewing gum, candy, snack food, frozen dessert, etc.), bread, noodles, pickle, dried fish, food boiled in soy sauce, soup, seasoning and the like by adding the composition for dementia of the present invention to various food starting materials and adding general food additives as necessary. It may also be a bottled food, canned food or retort pouch food.

As the above-mentioned food additive, manufacturing agent (brine, binding agent, etc.), thickening stabilizer (xanthan gum, sodium carboxymethylcellulose, etc.), gelling agent (gelatin, agar, carrageenan, etc.), gum base (vinyl acetate resin, jelutong, chicle, etc.), emulsifier (glycerol fatty acid ester, sucrose fatty acid ester, saponin, lecithin, etc.), preservative (benzoic acid, sodium benzoate, sorbic acid, potassium sorbate, ε-polylysine, etc.), antioxidant (ascorbic acid, erythorbic acid, catechin, etc.), glazing agent (shellac, paraffin wax, beeswax, etc.), fungicide (thiabendazole, fludioxonil, etc.), leavening agent (sodium hydrogen carbonate, glucono δ-lactone, alum, etc.), sweetener (aspartame, acesulfame potassium, licorice extract, etc.), bittering agent (caffeine, naringin, worm wood extract, etc.), acidulant (citric acid, tartaric acid, lactic acid, etc.), seasoning (sodium L-glutamate, disodium 5'-inosinate, etc.), colorant (annatto dye, turmeric dye, gardenia dye, etc.), flavor (synthetic flavor such as ethyl acetoacetate, anisealdehyde and the like, natural flavor such as orange, lavender and the like) and the like can be mentioned.

In the present invention, one or more kinds of the above-mentioned food additives can be used.

The food for dementia of the present invention may be preferably ingested by those requiring improvement in the symptoms of dementia, those with a risk of developing dementia, elderly people and middle- or late middle-aged persons who have a high risk of developing dementia and the like.

In addition, the food for dementia of the present invention can be widely ingested by subjects besides dementia patients and elderly people and middle- or late middle-aged persons who have a high risk of developing dementia for the purpose of preventing dementia.

Therefore, the food for dementia of the present invention can also be provided as food with health claims such as food for specified health uses, food with nutrient function claims, indicated functional food and the like, special purpose foods such as food for sick people, food for the elderly and the like, health supplement, dietary supplement and the like for preventing or improving dementia.

The food for dementia of the present invention is preferably ingested by the above-mentioned application subject such that the total amount of leucine and essential amino acid other than leucine per day is the above-mentioned ingestion amount per day.

Furthermore, the composition for depressive state of the present invention can be ingested by adding to various foods. The food to which the composition for depressive state of the present invention is added is not particularly limited, and may be any as long as it is a food in the form generally served for meals or dessert.

For example, the composition for depressive state of the present invention is added to drinks such as beverage water and the like, and a suitable flavor is added when desired, whereby a drink can be provided.

More specifically, the composition for depressive state of the present invention can be added, for example, to beverage water such as fruit juice drinks, sport drinks and the like; dairy products such as milk, yogurt and the like; confectionery such as jelly, chocolate, candy and the like, and the like.

The composition for depressive state of the present invention is preferably added to the above-mentioned various foods in amounts to be ingested per day such that the total amount of leucine and essential amino acid other than leucine is the above-mentioned dose per day.

The composition for depressive state of the present invention can be provided as a food (hereinafter to be also referred to as "the food for depressive state of the present invention" in the present specification) directly or by adding the above-mentioned general food additives as necessary and according to a general food production technique.

The food for depressive state of the present invention can be prepared as various forms such as liquid, suspension, emulsified liquid, gel, cream, powder, granule, sheet, capsule, tablet and the like.

Furthermore, the food for depressive state of the present invention can be prepared as various food forms such as beverage water (fruit juice drinks, sport drinks, coffee drinks, tea drinks, etc.), dairy product (lactic fermenting beverage, fermented milk, butter, cheese, yogurt, processed milk, defatted milk, etc.), meat product (ham, sausage, hamburger, etc.), fish meat processed seafood paste product (fish cake, tube-shaped fish sausage, deep-fried ball of fish paste, etc.), egg product (rolled Japanese-style omelette, steamed egg custard, etc.), confectionery (cookie, jelly, chewing gum, candy, snack food, frozen dessert, etc.), bread, noodles, pickle, dried fish, food boiled in soy sauce, soup, seasoning and the like by adding the composition for depressive state of the present invention to various food starting materials and adding the above-mentioned general food additives as necessary. It may also be a bottled food, canned food or retort pouch food.

The food for depressive state of the present invention may be preferably ingested by those requiring improvement of a depressive state. In addition, it can be widely ingested for the purpose of preventing a depressive state by those who may develop a depressive state by being exposed to various stresses.

Therefore, the food for depressive state of the present invention can also be provided as food with health claims such as food for specified health uses, food with nutrient function claims, indicated functional food and the like, special purpose foods such as food for sick people, food for the elderly and the like, health supplement, dietary supplement and the like for preventing or improving a depressive state.

The food for depressive state of the present invention is preferably ingested by the above-mentioned application subject such that the total amount of leucine and essential amino acid other than leucine per day is the above-mentioned ingestion amount per day.

Furthermore, the present invention also provides a method for preventing or improving dementia in a subject animal in need of prevention or improvement of dementia (hereinafter to be also referred to as the "preventive/improving method of dementia of the present invention" in the present specification).

The preventive/improving method of dementia of the present invention includes ingestion or administration to a subject animal in need of prevention or improvement of symptoms of dementia of leucine and essential amino acid other than leucine in amounts effective for preventing or improving the symptoms of dementia of the subject animal.

Of the symptoms seen as core symptoms of dementia, the preventive/improving method of dementia of the present invention is more effective for preventing or improving memory disorders and decline of cognitive function and particularly effective for preventing or improving Alzheimer-type dementia.

In the case of human, the preventive/improving method of dementia of the present invention is preferably applied to dementia patients requiring improvement of memory disorder and a decline of cognitive function, patients with a risk of developing dementia, and elderly people and middle- or late middle-aged persons who have a high risk of developing dementia and the like.

While the effective amount of leucine and essential amino acid other than leucine in the method for the prevention/improvement of dementia of the present invention is determined according to the kind, age, sex, level of symptoms of dementia, condition and the like of the subject animal, an amount similar to the above-mentioned ingestion amount or dose of the composition for dementia of the present invention for a human or a subject animal other than human can be ingested or administered at the frequency and period mentioned above.

Furthermore, the present invention also provides a method for preventing or improving a depressive state in a subject animal in need of prevention or improvement of a depressive state (hereinafter to be also referred to as the "preventive/improving method of depressive state of the present invention" in the present specification).

The preventive/improving method of depressive state of the present invention includes ingestion or administration to a subject animal in need of prevention or improvement of a depressive state of leucine and essential amino acid other than leucine in amounts effective for preventing or improving a depressive state of the subject animal.

The preventive/improving method of depressive state of the present invention is effective for preventing or improving a depressive state, and particularly effective for preventing or improving a depressive state caused by stress.

In the case of human, the preventive/improving method of depressive state of the present invention may be preferably applied to those showing a depressive state and requiring improvement thereof, or those who may develop a depressive state by being exposed to various stresses.

While the effective amount of leucine and essential amino acid other than leucine in the method for the prevention/improvement of depressive state of the present invention is determined according to the kind, age, sex, symptoms and the level of depressive state and the like of the subject animal, an amount similar to the above-mentioned ingestion amount or dose of the composition for depressive state of the present invention for a human or a subject animal other than human can be ingested or administered at the frequency and period mentioned above.

The subject animal in the present invention includes mammal (e.g., human, monkey, mouse, rat, guinea pig, hamster, rabbit, cat, dog, bovine, horse, donkey, swine, sheep, etc.), birds (e.g., duck, chicken, goose, turkey, etc.) and the like.

The ingestion or administration method of leucine and essential amino acid other than leucine in the present invention includes oral administration, enteral tube administration, administration by infusion and the like. Oral administration is preferable since convenient ingestion is possible without the need to perform under the guidance and supervision of a doctor at a medical institution.

Other features of the invention will become apparent in the course of the following descriptions of exemplary embodiments which are given for illustration of the invention and are not intended to be limiting thereof.

EXAMPLES

Example 1. Composition for Preventing or Improving Dementia

To afford the composition shown in Table 1, given amounts of respective components were weighed and mixed to prepare the composition for preventing or improving dementia of Example 1 (hereinafter sometimes to be referred to as "the composition of Example 1").

TABLE 1

| component | molar composition ratio (%) relative to total content of essential amino acids |
|---|---|
| L-leucine | 42.1 |
| L-isoleucine | 11.2 |

TABLE 1-continued

| component | molar composition ratio (%) relative to total content of essential amino acids |
|---|---|
| L-valine | 13.0 |
| L-threonine | 10.8 |
| L-lysine hydrochloride | 12.6 |
| L-methionine | 3.1 |
| L-histidine hydrochloride 1-hydrate | 1.1 |
| L-phenylalanine | 5.6 |
| L-tryptophan | 0.5 |

Experimental Example 1. Study of Action of Composition of Example 1 on Cognitive Function Using SAMP8 which is a senescence accelerated mouse model and learning and memory disorder mouse model, and SAMR1 which is a control mouse therefor (both 10-week-old, male) (purchased from CHARLES RIVER LABORATORIES JAPAN, INC.), an action of the composition of Example 1 on cognitive function was studied.

The respective mice of SAMP8 and SAMR1 were divided into 3 groups shown in Table 2 (n=16/group), reared from the day of arrival to the day of autopsy while allowing them to freely eat a feed containing 16% by weight of casein, and the composition (AL40) of Example 1 or deionized water (vehicle) was forcibly administered orally at 1 g/kg body weight twice per day (morning and evening) continuously (except Saturday and Sunday).

TABLE 2

| group | feed | n number |
|---|---|---|
| SAMR1 | feed containing 16 wt % casein + deionized water | 16 |
| SAMP8-vehicle | feed containing 16 wt % casein + deionized water | 16 |
| SAMP8-AL40 | feed containing 16 wt % casein + composition of Example 1 | 16 |

(1) Study of Action on Spatial Working Memory (Short Term Memory)

The mice of each group shown in Table 2 were subjected to a Y maze test as follows at 10, 13, 15, 17, 19, 21, and 23 weeks of age (oral administration of the composition of Example 1 or deionized water was stopped in the morning of the day of Y maze test).

Using a Y-shaped maze device, the mouse was placed on one of the arms thereof and allowed to move freely for 8 min, and the number of times the mouse entered the arm was recorded. At that time, the mouse was taken to have "entered" when the base of the tail entered the arm.

It is considered that the Y maze test can evaluate the spontaneous behavior and spatial working memory (short term memory) of mouse.

The spontaneous behavior of the mouse can be evaluated by the total number of times the mouse entered the arm. Using a group in which deionized water was orally administered to SAMP8 (SAMP8-vehicle) and a group in which the composition of Example 1 was orally administered to SAMP8 (SAMP8-AL40), changes in the total number of times the mouse entered the arm were compared based on the age and shown in FIG. 1 as mean±standard error of mean of 16 mice. For the measurement results of the total number of entries of the mouse, two-factor analysis of variance and multiple comparison test of Bonferroni were performed.

As an index of spatial working memory (short term memory), a value was obtained by dividing the number of three successive entries into different arms by the number obtained by subtracting 1 from the total number of arm entries, and then multiplying same by 100 (alternation behavior value). The mean±standard error of mean of 16 mice of the group in which deionized water was orally administered to SAMP8 at each week of age (SAMP8-vehicle), and the group in which the composition of Example 1 was orally administered to SAMP8 (SAMP8-AL40) were compared and shown in FIG. 2. As for the alternation behavior value, Student's t-test was performed.

As shown in FIG. 1, a significant difference was not observed in the arm entry number as an index of spontaneous behavior between the group in which deionized water was orally administered to SAMP8 (SAMP8-vehicle) and the group in which the composition of Example 1 was orally administered to SAMP8 (SAMP8-AL40) or according to the age in weeks.

Figure 2:
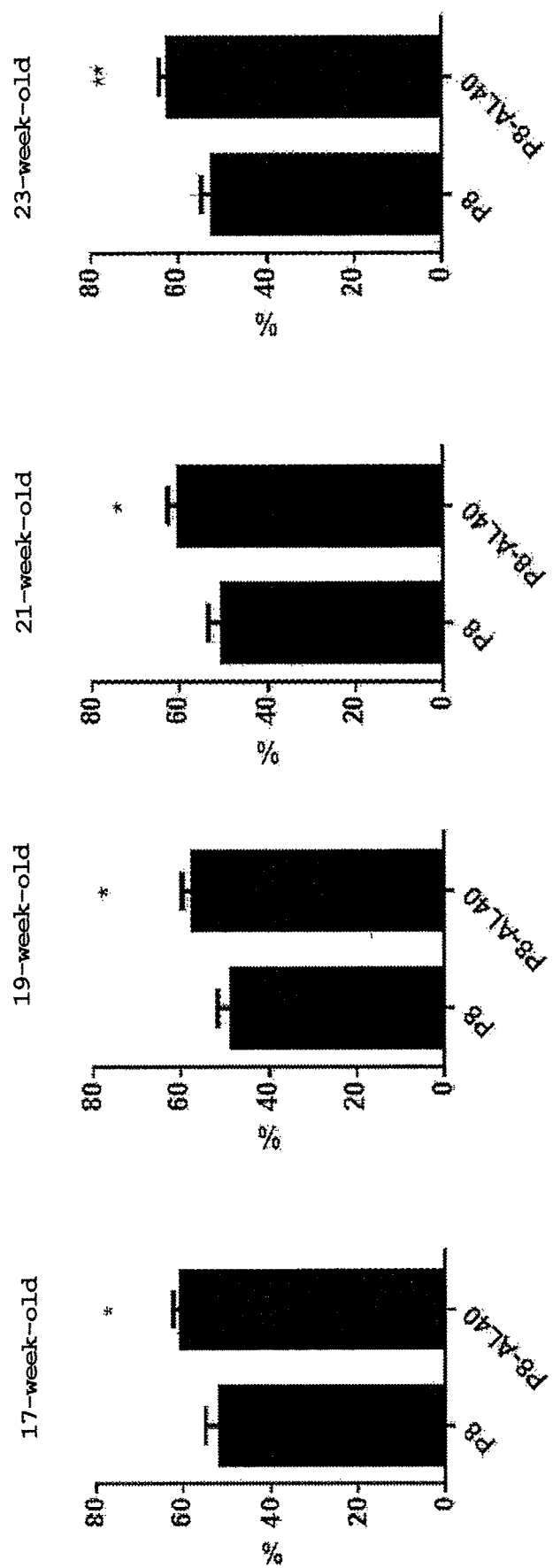
FIG. 2 shows the evaluation results of spatial working memory (short term memory) in the group in which deionized water was orally administered to SAMP8 (SAMP8-vehicle) and the group in which the composition of Example 1 was orally administered to SAMP8 (SAMP8-AL40) in the Y maze test in Experimental Example 1. In the Figure, "P8" shows the group in which deionized water was orally administered to SAMP8 (SAMP8-vehicle), and "P8-AL40" shows the group in which the composition of Example 1 was orally administered to SAMP8 (SAMP8-AL40). In the Figure, moreover, "*" shows that a significant difference was found at $P<0.05$ between the above-mentioned two groups, and "**" shows that a significant difference was found at $P<0.01$ between the above-mentioned two groups.

On the other hand, as shown in FIG. 2, in the group in which the composition of Example 1 was orally administered to SAMP8 (SAMP8-AL40) at 17-week-old, 19-week-old, 21-week-old and 23-week-old, the alternation behavior value increased significantly (P<0.05 for 17, 19, 21 weeks of age, P<0.01 for 23 weeks of age), thus suggesting that the spatial working memory (short term memory) is improved by oral administration of the composition of Example 1 as compared to the group in which the group in which deionized water was orally administered (SAMP8-vehicle).

(2) Evaluation of Effect on Short-Term Memory and Long-Term Memory

The mice of each group shown in Table 2 were subjected at 23 weeks of age to passive avoidance test as follows (oral administration of the composition of Example 1 or deionized water was stopped in the morning of the day of passive avoidance test).

(i) Using an apparatus composed of a light-dark compartment with an electric stimulation device in the dark compartment, a mouse was placed in the light compartment, and the time (latency) before entering the dark compartment was measured for maximum 120 seconds. When the mouse entered the dark compartment, the door was closed simultaneously with the entry, and an electric stimulation (2 mA, 1 sec) was applied. The entry into the dark compartment was defined to be the time point when the base of the tail entered the dark compartment.

(ii) The trial of (i) was repeated 5 times at maximum until the mouse remained in the light compartment for 120 seconds.

(iii) Three days later, the mouse was placed in the light compartment, and the time when the mouse stayed in the light compartment (retention time) was measured for maximum 300 seconds.

In the passive avoidance test, from the test performed on the first day, the time required for the entry into a dark compartment (transfer latency time) and the number of trials required for staying in a light compartment for 120 seconds (trials to criterion) in each trial can be evaluated as short term memory. Furthermore, long-term memory can be evaluated from the time of stay in the light compartment 3 days later (retention time).

Figure 3:
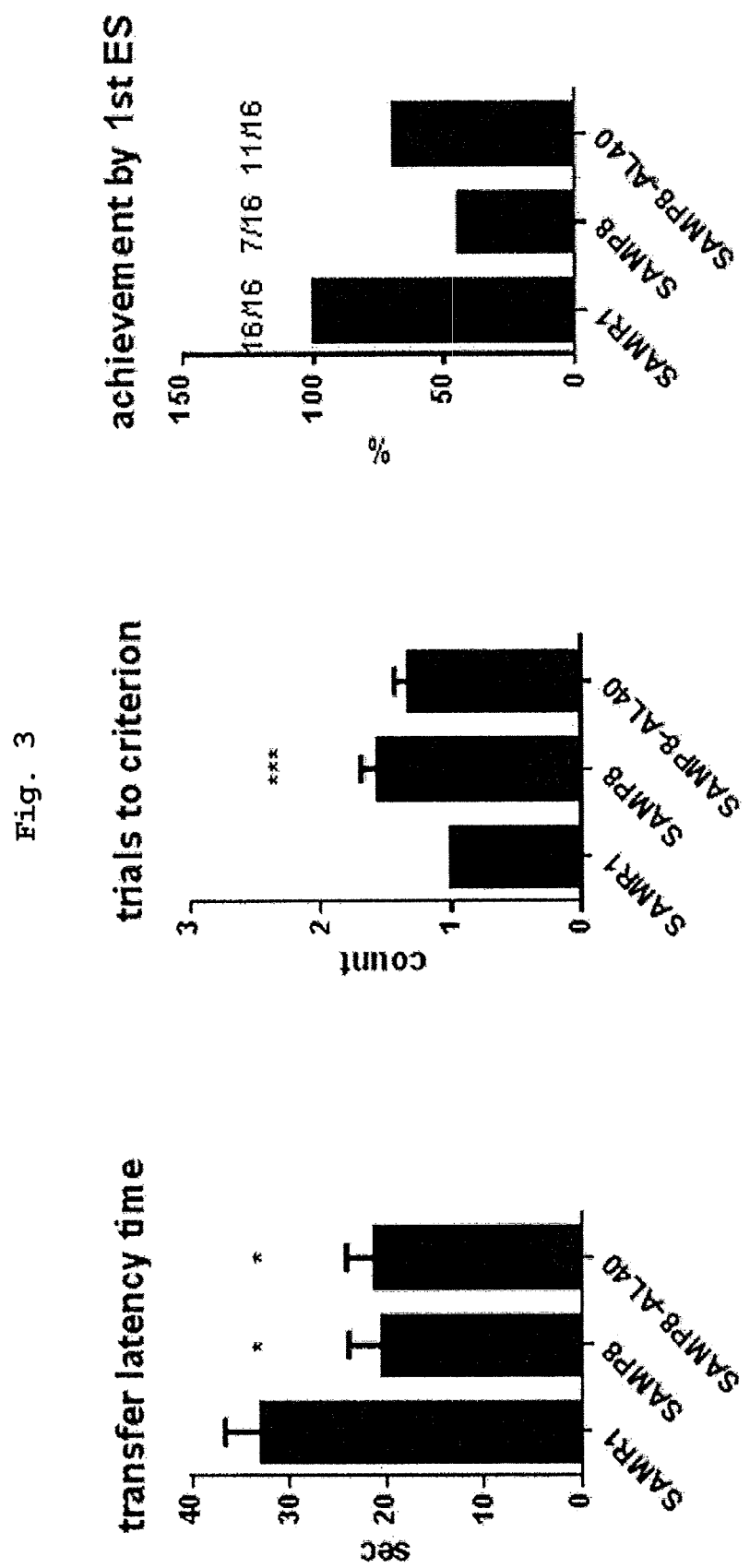
FIG. 3 shows the time required for entry into the dark compartment (transfer latency time) in the first trial, the number of trials required to make individuals stay in the light compartment for 120 seconds (trials to criterion) in the first trial, and the ratio of the number of individuals that stayed in the light compartment for 120 seconds in the second trial, in the group in which deionized water was orally administered to SAMR1 (SAMR1), the group in which deionized water was orally administered to SAMP8 (SAMP8-vehicle) and the group in which the composition of Example 1 was orally administered to SAMP8 (SAMP8-AL40) in the passive avoidance test in Experimental Example 1. In the Figure, "SAMP8" shows the group in which deionized water was orally administered to SAMP8 (SAMP8-vehicle). In the Figure, moreover, "*" shows that a significant difference from SAMR1 was found at $P<0.05$, and "***" shows that a significant difference from SAMR1 was found at $P<0.005$.

For the mice in each group, the time required for the entry into a dark compartment in the first trial (transfer latency time) and the number of trials required for staying in a light compartment for 120 seconds (trials to criterion) are shown each as mean±standard error of mean of 16 mice in FIG. 3.

Furthermore, the number of mice that stayed in the light compartment for 120 seconds in the second trial, that is, the ratio of the number of mice that memorized that the dark compartment is scary by one electric stimulation (achievement by 1st ES) is shown together in FIG. 3. The numerical values in the Figure show the number of mice in each group that stayed in the light compartment for 120 seconds in the second trial.

Figure 4:
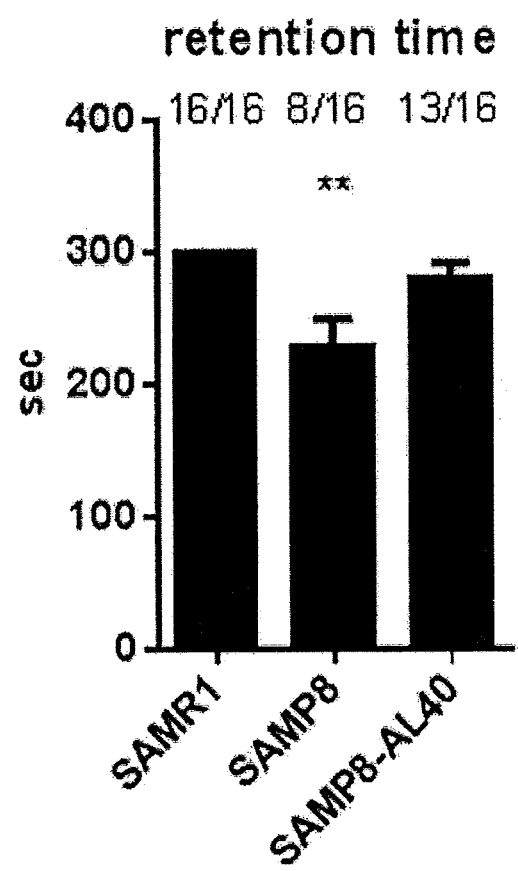
FIG. 4 shows the time of stay in the light compartment 3 days later (retention time) in the group in which deionized water was orally administered to SAMR1 (SAMR1), the group in which deionized water was orally administered to SAMP8 (SAMP8-vehicle) and the group in which the composition of Example 1 was orally administered to SAMP8 (SAMP8-AL40) in the passive avoidance test in Experimental Example 1. In the Figure, "SAMP8" shows the group in which deionized water was orally administered to SAMP8 (SAMP8-vehicle). In the Figure, moreover, "**" shows that a significant difference from SAMR1 was found at $P<0.01$.

The time of stay in the light compartment 3 days later (retention time) is shown in FIG. 4 as mean±standard error of mean of 16 mice. The numerical values in the Figure show the number of mice in each group that stayed in the light compartment for 300 seconds.

As for the time required for the entry into a dark compartment in the first trial (transfer latency time) and the number of trials required for staying in a light compartment for 120 seconds (trials to criterion) and the time of stay in the light compartment 3 days later (retention time), Dunnett's multiple comparison test was performed.

As shown in FIG. 3, as compared to the group in which deionized water was orally administered to SAMR1 (SAMR1), the time required for the entry into a dark compartment (transfer latency time) in the first trial was found to be significantly (P<0.05) shorter in other two groups.

In addition, the number of trials required for staying in a light compartment for 120 seconds (trials to criterion) was one in the group in which deionized water was orally administered to SAMR1 (SAMR1), and more than one and less than two both in the group in which deionized water was orally administered to SAMP8 (SAMP8-vehicle) and the group in which the composition of Example 1 was orally administered to SAMP8 (SAMP8-AL40). However, the aforementioned number of trials significantly (P<0.005) increased in the group in which deionized water was orally administered to SAMP8 (SAMP8-vehicle) as compared to the group in which deionized water was orally administered to SAMR1 (SAMR1), whereas the aforementioned number of trials decreased in the group in which the composition of Example 1 was orally administered to SAMP8 (SAMP8-AL40) to the extent that a significant difference from the group in which deionized water was orally administered to SAMR1 (SAMR1) was not found.

The ratio of the number of mice that memorized that the dark compartment is scary by one electric stimulation (achievement by 1st ES) clearly increased in the group in which the composition of Example 1 was orally administered to SAMP8 (SAMP8-AL40) as compared to the group in which deionized water was orally administered to SAMP8 (SAMP8-vehicle).

Furthermore, as shown in FIG. 4, the time of stay in the light compartment 3 days later (retention time) also significantly (P<0.01) decreased in the group in which deionized water was orally administered to SAMP8 (SAMP8-vehicle) as compared to the group in which deionized water was orally administered to SAMR1 (SAMR1). However, in the group in which the composition of Example 1 was orally administered to SAMP8 (SAMP8-AL40), the time increased to the same level as in the group in which deionized water was orally administered to SAMR1 (SAMR1).

From the results of the above-mentioned passive avoidance test, it was suggested that the composition of Example 1 of the present invention may improve both the short term memory and long term memory.

(3) Evaluation of Effect on Hippocampal Neuron

The mice of each group shown in Table 2 were autopsied at 23 weeks of age after completion of the above-mentioned respective tests, and hippocampal section was produced and Klüver-Barrera stained.

Under a microscope ("DFC350FX", manufactured by Leica, magnification: 20 times), digital filming of the CA1 region was performed and the number of neurons per a fixed pixel was measured for the image by using an analysis software ("image-J", an open resource produced by NIH (National Institutes of Health)). Then, the number of pixels was converted to square millimeters, and the number of neurons per unit area was calculated. The calculated number of neurons is shown as mean±standard error of mean of 16 mice and Dunnett's multiple comparison test was performed.

Figure 5:
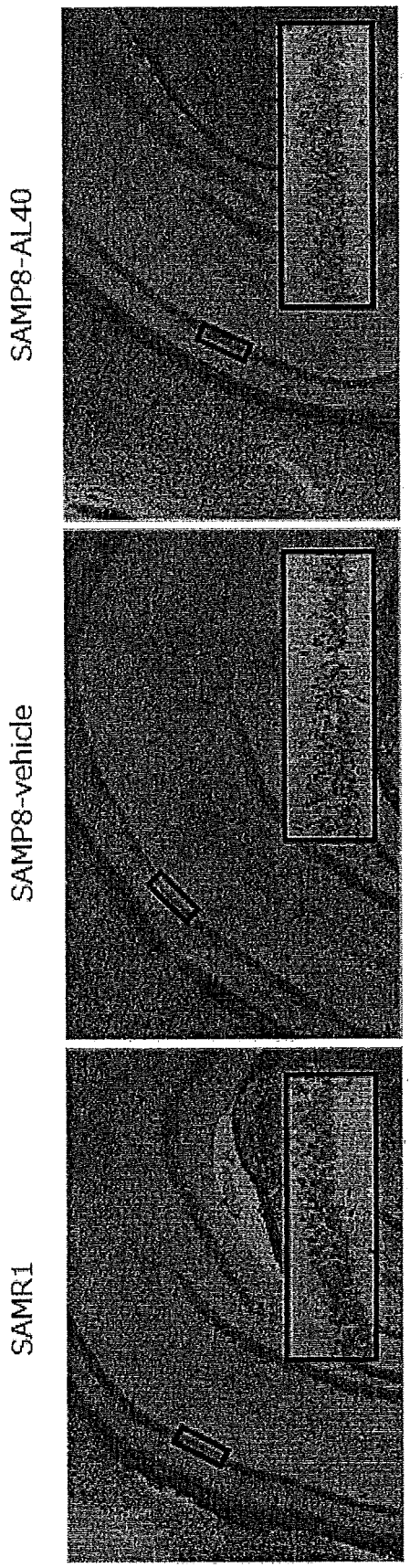
FIG. 5 shows Klüver-Barrera staining image of a hippocampus section in the group in which deionized water was orally administered to SAMR1 (SAMR1), the group in which deionized water was orally administered to SAMP8 (SAMP8-vehicle) and the group in which the composition of Example 1 was orally administered to SAMP8 (SAMP8-AL40) in Experimental Example 1.
Figure 6:
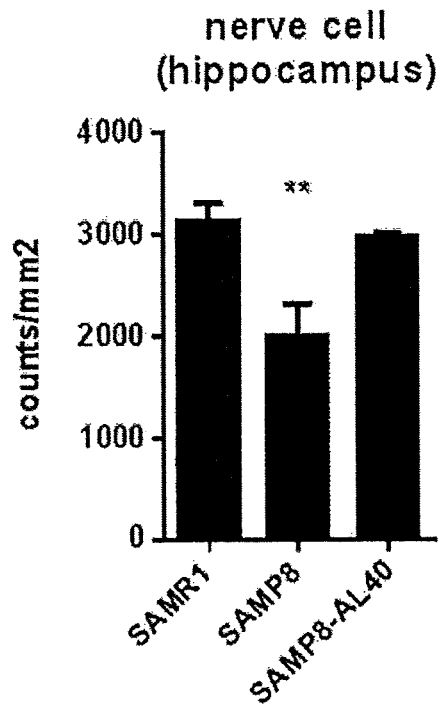
FIG. 6 shows the measurement results of the number of neurons in the hippocampus section in the group in which deionized water was orally administered to SAMR1 (SAMR1), the group in which deionized water was orally administered to SAMP8 (SAMP8-vehicle) and the group in which the composition of Example 1 was orally administered to SAMP8 (SAMP8-AL40) in Experimental Example 1. In the Figure, "SAMP8" shows the group in which deionized water was orally administered to SAMP8 (SAMP8-vehicle). In the Figure, moreover, "**" shows that a significant difference from SAMR1 was found at $P<0.01$.

The Klüver-Barrera staining image under the microscope is shown in FIG. 5 and the measurement results of the number of neurons are shown in FIG. 6.

As shown in FIG. 5 and FIG. 6, a significant (P<0.01) decrease in neurons in hippocampal CA1 region was found in the group in which deionized water was orally administered to SAMP8 (SAMP8-vehicle) as compared to the group in which deionized water was orally administered to SAMR1 (SAMR1). In contrast, in the group in which the composition of Example 1 was orally administered to SAMP8 (SAMP8-AL40), a decrease in the neurons was not found and the presence of neurons at the same level as in the group in which deionized water was orally administered to SAMR1 (SAMR1) was confirmed.

Therefore, the composition of Example 1 of the present invention suppressed the loss of neuron in hippocampus, and the possibility of suppressing memory disorders and a decline of cognitive function was suggested.

(4) Evaluation of Effect on Acetylcholine Content of Prefrontal Cortex

Figure 7:
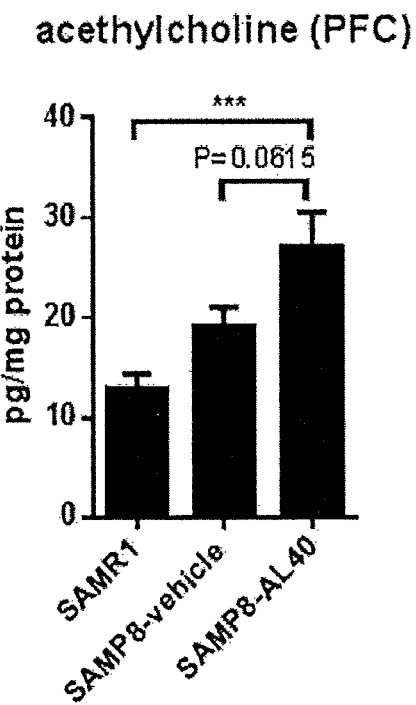
FIG. 7 shows the content of acetylcholine in the homogenate of prefrontal cortex (PFC) in the group in which deionized water was orally administered to SAMR1 (SAMR1), the group in which deionized water was orally administered to SAMP8 (SAMP8-vehicle) and the group in which the composition of Example 1 was orally administered to SAMP8 (SAMP8-AL40) in Experimental Example 1. In the Figure, "***" shows that a significant difference from SAMR1 was found at $P<0.005$.

The mice of each group shown in Table 2 were autopsied at 23 weeks of age after completion of the above-mentioned respective tests, and a homogenate of prefrontal cortex (PFC) was prepared. Using ELISA (Enzyme-Linked Immunosorbent Assay) kit, acetylcholine content was quantified, and the acetylcholine content per 1 mg protein in the homogenate of prefrontal cortex (PFC) is shown in FIG. 7 (mean±standard error of mean of 16 mice). The quantification results were applied to Holm-Sidak's multiple comparison test.

As shown in FIG. 7, in the group in which the composition of Example 1 was orally administered to SAMP8 (SAMP8-AL40), it was found that the acetylcholine content in PFC significantly (P<0.005) increased as compared to the group in which deionized water was orally administered to SAMR1 (SAMR1). In addition, a tendency toward increase (P=0.0615) was also shown as compared to the group in which deionized water was orally administered to SAMP8 (SAMP8-vehicle).

Acetylcholine is a neurotransmitter known to decrease in the brain of patients with Alzheimer-type dementia.

Therefore, the above-mentioned evaluation results suggest that the composition of Example 1 of the present invention may improve Alzheimer-type dementia.

Example 2. Composition for Preventing or Improving Depressive State

To afford the composition shown in Table 3, given amounts of respective components were weighed and mixed to prepare the composition for preventing or improving depressive state of Example 2 (hereinafter sometimes to be referred to as "the composition of Example 2").

TABLE 3

| component | ratio (mol %) of molar composition relative to total content of essential amino acids |
|---|---|
| L-leucine | 42.1 |
| L-isoleucine | 11.2 |
| L-valine | 13.0 |
| L-threonine | 10.8 |
| L-lysine hydrochloride | 12.6 |
| L-methionine | 3.1 |
| L-histidine | 1.1 |
| L-phenylalanine | 5.6 |
| L-tryptophan | 0.5 |

Experimental Example 2. Study of Effect of Composition of Example 2 on Depressive State Using BL6J mouse (10-week-old, male) (purchased from CHARLES RIVER LABORATORIES JAPAN, INC.), the effect of the composition of Example 2 on a depressive state was studied.

The BL6J mice were divided into 3 groups shown in Table 4 (n=12/group), KN209 breeding room was set as a dark compartment from 7 to 19 and a light compartment from 19 to 7 and one mouse was placed and reared in one cage and reared from the day of arrival to the day of autopsy while allowing them to freely eat a feed containing 16% by weight of casein, and the composition (AL40) of Example 2 or deionized water (vehicle) was forcibly administered orally at 1 g/kg body weight twice per day (morning and evening) continuously (except Saturday and Sunday). During the rearing period, various stresses (CUS: chronic unpredictable stress) were applied according to the stress load menu shown in FIG. 8 to the group in which deionized water was orally administered to stressed mouse (CUS-vehicle), and the group in which the composition of Example 2 was orally administered to stressed mouse (CUS-AL40).

TABLE 4

| group | presence or absence of stress load, feed | n number |
|---|---|---|
| CUS-vehicle | with stress load, 16 wt % casein-containing feed + deionized water | 12 |
| CUS-AL40 | with stress load, 16 wt % casein-containing feed + composition of Example 1 | 12 |
| Free-vehicle | without stress load, 16 wt % casein-containing feed + deionized water | 12 |

Figure 9:
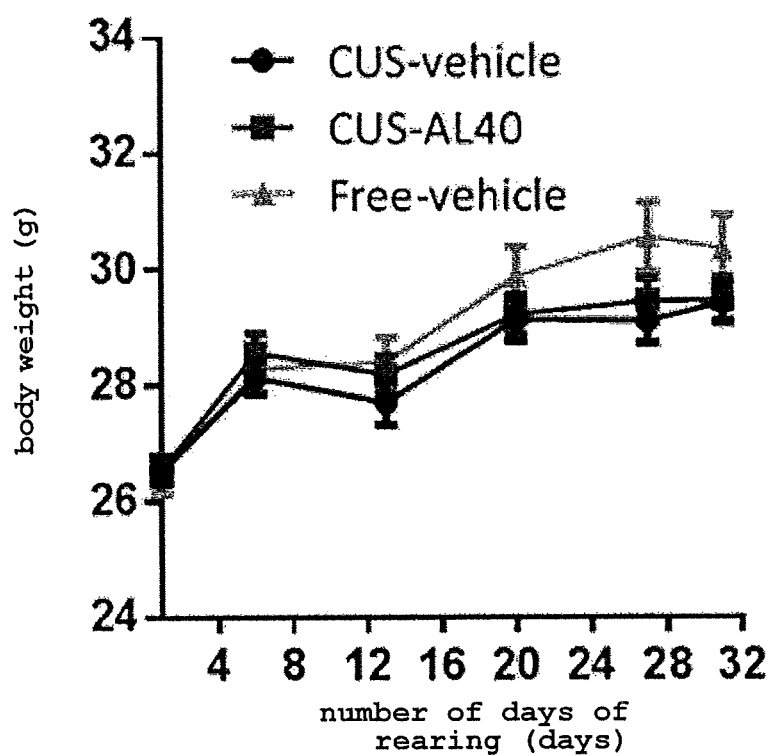
FIG. 9 shows changes in the body weight of the mice in each group in Experimental Example 2.

The body weight of each mouse was measured on days 6, 13, 20, 27, and 31 of rearing, and mean±standard error of mean of each group is shown in FIG. 9. In addition, increase in the body weight of mice in each group (difference in body weight between day 31 of rearing from that on the day of start of rearing) is shown in FIG. 10.

Figure 10:
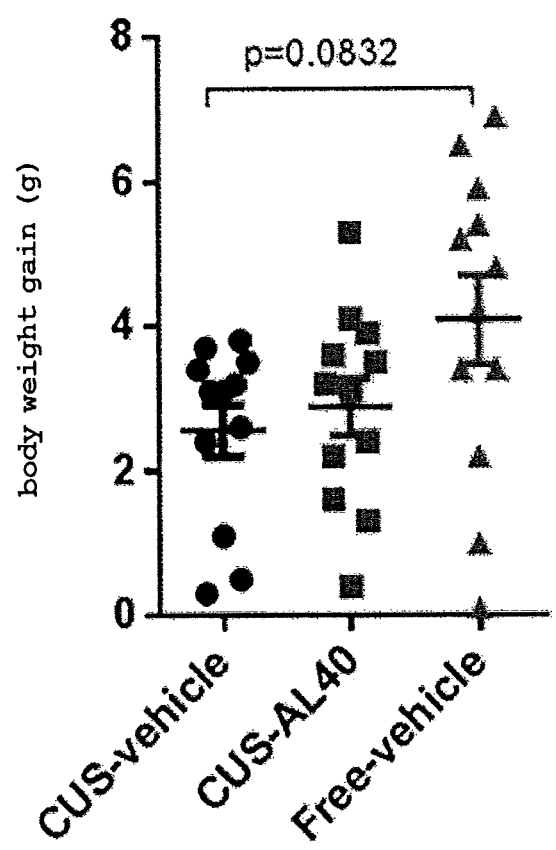
FIG. 10 shows difference in the body weight of the mice in each group between day 31 of rearing and the day when the rearing was started in Experimental Example 2.

As shown in FIG. 9 and FIG. 10, an increase in the body weight was tended to be suppressed in the group in which deionized water was orally administered to stress-loaded mice (CUS-vehicle) and the group in which the composition of Example 2 was orally administered to stress-loaded mouse (CUS-AL40), as compared to the group in which deionized water was orally administered to mouse without stress (Free-vehicle).

On day 30 of rearing, a forced swimming test (1 L cylinder, room temperature, 6 minutes) was performed for the mice of each group.

In the forced swimming test, a mouse placed in a water tank first struggles, swims around, but thereafter stops moving while floating in water with only the tip of the nose sticking out from the water surface. The time during which the mouse does not move (immobility time) is taken as an index of a depressive state.

Figure 11:
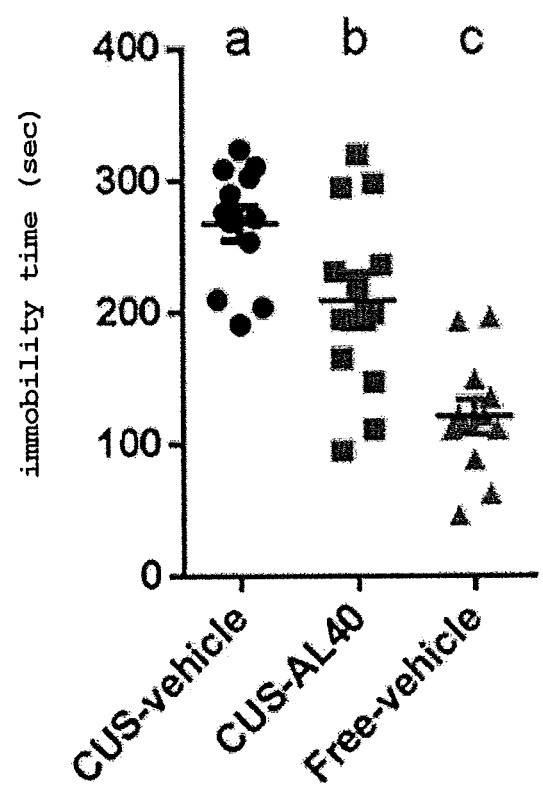
FIG. 11 shows the measurement results of immobility time of each group in the forced swimming test in Experimental Example 2. In the Figure, different letters of "a", "b" and "c" show the presence of a significant difference among the respective groups.

The immobility time of the mice of each group was measured and the results are shown in FIG. 11. The measurement results were applied to Holm-Sidak's multiple comparison test.

As shown in FIG. 11, immobility time significantly ($P<0.0001$) increased in the group in which deionized water was orally administered to stress-loaded mice (CUS-vehicle) and the group in which the composition of Example 2 was orally administered to stress-loaded mouse (CUS-AL40), as compared to the group in which deionized water was orally administered to mouse without stress (Free-vehicle). However, it was found that the immobility time was significantly ($P<0.05$) short in the group in which the composition of Example 2 was orally administered to stress-loaded mouse (CUS-AL40), as compared to the group in which deionized water was orally administered to stress-loaded mice (CUS-vehicle).

The above-mentioned evaluation results suggest that the composition of Example 2 of the present invention may improve the depressive state caused by stress.

INDUSTRIAL APPLICABILITY

As described in detail above, a composition for preventing or improving dementia can be provided according to the present invention.

The composition for preventing or improving dementia of the present invention effectively prevents or improves memory disorders, is also effective for the suppression or improvement of a decline of cognitive function, and particularly effective for preventing or improving Alzheimer-type dementia.

Furthermore, the composition for preventing or improving dementia of the present invention is highly safe and suitable for continuous ingestion or administration.

According to the present invention, a composition for preventing or improving a depressive state, which can favorably prevent or improve the depressive state can be provided.

The composition for preventing or improving a depressive state of the present invention is particularly effective for preventing or improving a depressive state caused by stress.

Furthermore, the composition for preventing or improving a depressive state of the present invention has high safety and is suitable for continuous ingestion or administration.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for preventing or improving dementia, comprising administering to a subject in need thereof an effective amount of a composition comprising one or more kinds of essential amino acids other than leucine and 35 mol % to 66 mol % of leucine, relative to the total content of essential amino acids.

2. The method according to claim 1, wherein said composition comprises said leucine in an amount of 35 mol % to 57 mol %, relative to the total content of essential amino acids.

3. The method according to claim 1, wherein said one or more kinds of essential amino acids other than leucine are isoleucine, valine, threonine, lysine, methionine, histidine, phenylalanine, and tryptophan.

4. The method according to claim 3, wherein a molar composition ratio of the content of each amino acid in said composition, relative to the total content of essential amino acids, falls within the following numerical values:
   leucine: 35 mol % to 66 mol %
   isoleucine: 5 mol % to 15 mol %
   valine: 5 mol % to 15 mol %
   threonine: 7 mol % to 14 mol %
   lysine: 8 mol % to 16 mol %
   methionine: 2 mol % to 10 mol %
   histidine: 0.1 mol % to 3.5 mol %
   phenylalanine: 2.5 mol % to 8 mol %
   tryptophan: 0.1 mol % to 2 mol %.

5. The method according to claim 1, which prevents or improves a memory disorder.

6. The method according to claim 1, which suppresses a decline of cognitive function or improves cognitive function.

7. The method according to claim 1, wherein the dementia is Alzheimer-type dementia.

* * * * *